(12) United States Patent
Boock et al.

(10) Patent No.: US 12,087,469 B2
(45) Date of Patent: Sep. 10, 2024

(54) COATING A WORKING WIRE FOR A CONTINUOUS BIOLOGICAL SENSOR

(71) Applicant: Allez Health Inc., Carlsbad, CA (US)

(72) Inventors: Robert James Boock, Carlsbad, CA (US); Huashi Zhang, San Juan Capistrano, CA (US); Wei Gu, San Diego, CA (US)

(*) Notice: Subject to any disclaimer, the term of this patent is extended or adjusted under 35 U.S.C. 154(b) by 296 days.

(21) Appl. No.: 17/659,267

(22) Filed: Apr. 14, 2022

(65) Prior Publication Data

US 2023/0335315 A1    Oct. 19, 2023

(51) Int. Cl.
| | |
|---|---|
| *H01B 13/32* | (2006.01) |
| *B05D 1/18* | (2006.01) |
| *A61B 5/145* | (2006.01) |

(52) U.S. Cl.
CPC .......... *H01B 13/328* (2013.01); *B05D 1/18* (2013.01); *A61B 5/14532* (2013.01)

(58) Field of Classification Search
CPC ............................... B05D 1/18; H01B 13/328
See application file for complete search history.

(56) References Cited

U.S. PATENT DOCUMENTS

| | | | |
|---|---|---|---|
| 10,624,568 B2 | 4/2020 | Böhm et al. | |
| 2014/0348703 A1 | 11/2014 | Thomas et al. | |
| 2014/0378793 A1 | 12/2014 | Kamath et al. | |
| 2017/0146732 A1* | 5/2017 | Botelho | ............. G02B 6/02395 |
| 2017/0188916 A1 | 7/2017 | Wang et al. | |
| 2018/0094290 A1 | 4/2018 | Feldman et al. | |
| 2019/0320947 A1 | 10/2019 | Chen et al. | |
| 2021/0088364 A1* | 3/2021 | Robert | ...................... B05D 1/02 |
| 2021/0154340 A1* | 5/2021 | Kelson | ..................... A61L 31/10 |
| 2022/0095970 A1* | 3/2022 | McCarthy | .......... A61B 5/14532 |
| 2022/0313124 A1 | 10/2022 | Garcia et al. | |

FOREIGN PATENT DOCUMENTS

| | | |
|---|---|---|
| CN | 113340969 A | 9/2021 |
| EP | 3912551 A4 | 11/2021 |
| WO | 2017117472 A1 | 7/2017 |
| WO | 2022044018 A2 | 3/2022 |

OTHER PUBLICATIONS

Griffin, Jon, Dip Coating: Practical Guide to Theory and Troubleshooting, Ossila Ltd, Dec. 15, 2021, 28 pages, Sheffield, UK.
European Search Report dated Jul. 19, 2023 for European Patent Office Patent Application No. 23167552.1.
International Search Report and Written Opinion dated Jan. 22, 2024 for PCT Patent Application No. PCT/IB2023/060539.

* cited by examiner

*Primary Examiner* — Nathan T Leong
(74) *Attorney, Agent, or Firm* — MLO, a professional corp.

(57) ABSTRACT

Methods for coating a working wire for a continuous biological sensor include providing a plurality of wires in a fixture and dipping the plurality of wires into a coating solution according to parameters for a dipping process. A plurality of diameters is measured along a length of at least two coated wires of the plurality of wires in the fixture, using an automated measurement system, as in an in-line process. A controller that is in communication with the automated measurement system determines a thickness difference, the thickness difference being a difference between a thickness setpoint and an aggregate criteria for the plurality of diameters. The controller calculates adjusted parameters for the dipping process based on the thickness difference.

16 Claims, 10 Drawing Sheets

COATING A WORKING WIRE FOR A CONTINUOUS BIOLOGICAL SENSOR

BACKGROUND

Medical patients often have diseases or conditions that require the measurement and reporting of biological conditions. For example, if a patient has diabetes, it is important that the patient have an accurate understanding of the level of glucose in their system. Traditionally, diabetes patients have monitored their glucose levels by sticking their finger with a small lance, allowing a drop of blood to form, and then dipping a test strip into the blood. The test strip is positioned in a handheld monitor that performs an analysis on the blood and visually reports the measured glucose level to the patient. Based upon this reported level, the patient makes important decisions on what food to consume, or how much insulin to inject. Although it would be advantageous for the patient to check glucose levels many times throughout the day, many patients fail to adequately monitor their glucose levels due to the pain and inconvenience. As a result, the patient may eat improperly or inject either too much or too little insulin. Either way, the patient has a reduced quality of life and increased chance of doing permanent damage to their health and body. Diabetes is a devastating disease that if not properly controlled can lead to detrimental physiological conditions such as kidney failure, skin ulcers, bleeding in the eyes and eventually blindness, and pain and the eventual amputation of limbs.

Blood glucose levels can significantly rise or lower quickly due to various causes, which can further complicate glucose monitoring. Accordingly, a single glucose measurement provides only a snapshot of the instantaneous level in a patient's body. Such a single measurement provides little information about how the patient's use of glucose is changing over time, or how the patient reacts to specific dosages of insulin. Even a patient that is adhering to a strict schedule of strip testing will likely be making incorrect decisions as to diet, exercise, and insulin injection. This is exacerbated by a patient that is less consistent on their strip testing. To give the patient a more complete understanding of their diabetic condition and to get a better therapeutic result, some diabetic patients are now using continuous glucose monitoring.

Monitoring of glucose levels is critical for diabetes patients. Continuous glucose monitoring (CGM) sensors are a type of device in which glucose is measured from fluid sampled in an area just under the skin multiple times a day. CGM devices typically involve a small housing in which the electronics are located, and which is adhered to the patient's skin to be worn for a period of time. A small needle within the device delivers the subcutaneous sensor which is often electrochemical. Depending upon the patient's condition, continuous glucose monitoring may be performed at different intervals. For example, some continuous glucose monitors may be set to take multiple readings per minute, whereas in other cases the continuous glucose monitor can be set to take readings every hour or so.

Electrochemical glucose sensors operate by using electrodes which typically detect an amperometric signal caused by oxidation of enzymes during conversion of glucose to gluconolactone. The amperometric signal can then be correlated to a glucose concentration. Two-electrode (also referred to as two-pole) designs use a working electrode and a reference electrode, where the reference electrode provides a reference against which the working electrode is biased. The reference electrodes effectively complete the electron flow in the electrochemical circuit. Three-electrode (or three-pole) designs have a working electrode, a reference electrode, and a counter electrode. The counter electrode replenishes ionic loss at the reference electrode and is part of the ionic circuit.

Unfortunately, the cost of using a continuous glucose monitor can be prohibitive for many patients who could benefit greatly from its use. A continuous glucose monitor has two main components. First, there is a housing for the electronics, processor, memory, wireless communication, and power. The housing is typically reusable over extended periods of time, such as months. This housing then connects or communicates to a disposable CGM sensor that is adhered to the patient's body, which typically uses an introducer needle to subcutaneously insert the sensor into the patient. This sensor must be replaced, sometimes as often as every three days, and likely at least once every other week. Thus, the cost to purchase new disposable sensors represents a significant financial burden to patients and insurance companies. Because of this, a substantial number of patients who could benefit from continuous glucose monitoring are not able to use such systems and are forced to rely on the less reliable finger stick monitoring. The working wires are conventionally time consuming to make due to the number of process steps involved and that they must be precisely manufactured to produce accurate results. Accordingly, a new way of efficiently manufacturing working wires is needed.

SUMMARY

In some embodiments, a method for coating a working wire for a continuous biological sensor includes providing a plurality of wires in a fixture and dipping the plurality of wires into a coating solution according to parameters for a dipping process. A plurality of diameters is measured along a length of at least two coated wires of the plurality of wires in the fixture, using an automated measurement system, as in an in-line process. A controller that is in communication with the automated measurement system determines a thickness difference, the thickness difference being a difference between a thickness setpoint and an aggregate criteria for the plurality of diameters. The controller calculates adjusted parameters for the dipping process based on the thickness difference.

DETAILED DESCRIPTION

Embodiments disclose systems and processes for manufacturing working wires for a continuous biological sensor, that reduce cost and improve accuracy and efficiency compared to known art. The continuous biological sensor may be, for example, a continuous glucose monitor, in which the working wire includes an enzyme layer to detect the level of glucose in a patient's blood. In other embodiments, the biological sensor can be a metabolic sensor for measuring other metabolic characteristics such as ketones or fatty acids. The sensor uses a working wire (i.e., electrode for the sensor) that has a core and several concentrically formed membrane layers.

In embodiments, an automated system measures dimensions of working wires while they are progressing through a dipping process and uses the measurements to adjust dipping parameters in real time. The measurement system takes multiple measurements along a length of the working wires and also measures multiples wires that are mounted in a carrier. By providing thorough monitoring of coating thicknesses in an in-line manner while the layers are being built, more efficient and accurate dip coating of working wires is achieved. The in-line manner involves taking measurements during a dipping process, after each dip for creating a layer. In contrast, conventional methods typically take measurements after all the layers on the wire have been applied. The present methods adjust dipping parameters based on the measured thicknesses and on other factors that are monitored such as the temperature or viscosity of the coating solution. In some embodiments, environmental factors can also be analyzed along with the coated wire measurements to adjust dipping parameters. In further embodiments, coating solutions of different viscosities can be provided for the dipping process, and the system can choose which viscosity to use based on the measurements. The systems and methods may optimize the manufacturing process, such as by reducing the number of dips required to achieve a desired coating thickness within a target window.

Figure 1:
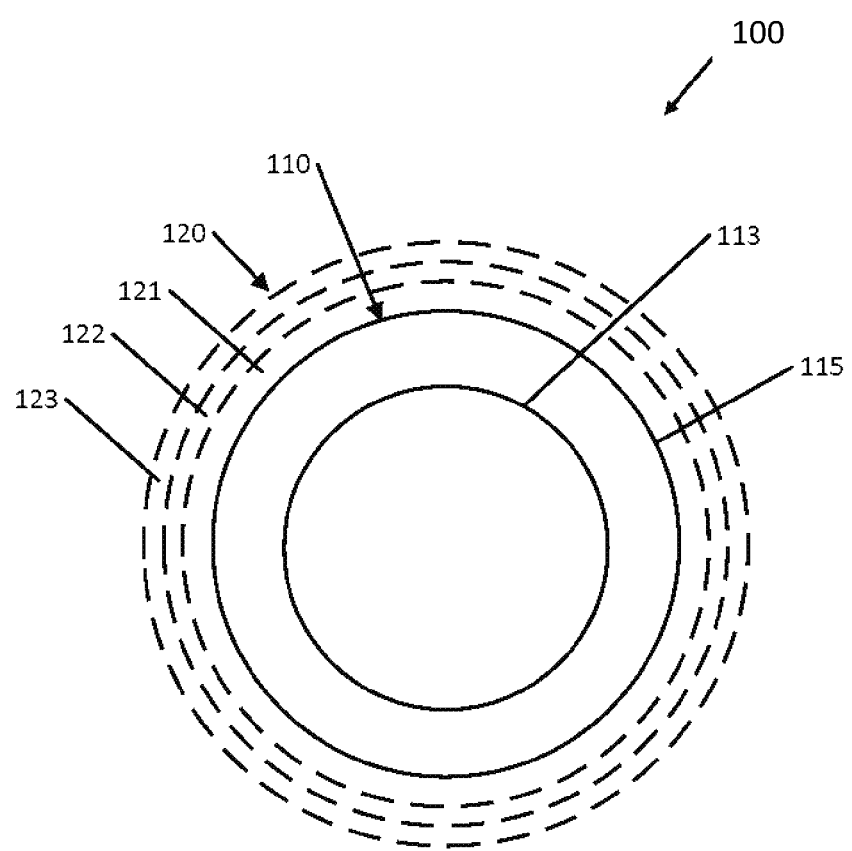
FIG. 1 is a not-to-scale cross-sectional view of a working wire, in accordance with some embodiments.

Referring to FIG. 1, a cross-sectional view of a working wire 100 is illustrated in accordance with some embodiments. In this example, the working wire 100 is an elongated wire having a circular cross-section. It will be understood that other cross-sections may be used, such as square, rectangular, triangular, or other geometric shapes. Furthermore, the working wire 100 may take other forms, such as a plate or ribbon. The working wire is used as a working electrode of a continuous biological sensor, such as a working electrode of a continuous glucose monitor.

In the illustrated example, the working wire 100 has a substrate 110 onto which biological membranes 120 may be disposed. The types of biological membranes that may be used are well-known and will not be described in detail herein. In one example as illustrated, the biological membranes 120 include an interference membrane 121 (which may also be referred to as an interference layer) on the substrate 110, an enzyme membrane 122 (i.e., enzyme layer) on the interference membrane 121, and a glucose limiting membrane 123 (i.e., glucose limiting layer) on the enzyme membrane 122. In some embodiments, a protective or outer coating may be optionally applied over the glucose limiting membrane 123. Although the working wire 100 is illustrated as having three membranes 120, it will be understood that the membranes 120 may be more or fewer in number.

The substrate 110 may be comprised of a core 113 with an outer layer 115. In the example of FIG. 1, the core 113 is an elongated wire that is dense, ductile, very hard, easily fabricated, highly conductive of heat and electricity, and may also be resistant to corrosion. Example materials for core 113 include tantalum, carbon, or Co—Cr alloys. The core 113 may have the outer layer 115, such as of platinum, deposited or applied using an electroplating process. It will be understood that other processes may be used for applying the outer layer 115 to the core 113. For a glucose monitor, the platinum outer layer facilitates a reaction where the hydrogen peroxide reacts to produce water and hydrogen ions, and two electrons are generated. The electrons are drawn into the platinum by a bias voltage placed across the platinum wire and a reference electrode. In this way, the magnitude of the electrical current flowing in the platinum is intended to be related to the number of hydrogen peroxide reactions, which in turn is proportional to the number of glucose molecules oxidized. A measurement of the electrical current on the platinum wire can thereby be associated with a particular level of glucose in the patient's blood or interstitial fluid (ISF).

The core 113, outer layer 115, interference membrane 121, and enzyme membrane 122 form key aspects of working wire 100. Other layers and/or membranes may be added depending upon the biological substance being tested for, and application-specific requirements. In some cases, the core 113 may have an inner core portion (not shown). For example, if the substrate (core 113) is made from tantalum, an inner core of titanium or titanium alloy may be included to provide additional strength and straightness.

In some cases, one or more membranes (i.e., layers) may be provided over the enzyme membrane 122. For example, a glucose limiting membrane 123 may be layered on top of the enzyme membrane 122. This glucose limiting membrane 123 may limit the number of glucose molecules that can pass through the glucose limiting membrane 123 and into the enzyme membrane 122. The glucose limiting membrane 123 can be configured as described in U.S. patent application Ser. No. 16/375,877, entitled "Enhanced Glucose Limiting Membrane for a Working Electrode of a Continuous Biological Sensor," which is owned by the assignee of the present disclosure and is incorporated herein by reference as if set forth in its entirety. In some cases, the addition of the glucose limiting membrane 123 has been shown to enable better performance of the overall working wire 100.

An interference membrane 121 is applied over the outer layer 115. The interference membrane 121 may be disposed between the enzyme membrane 122 and the outer layer 115. This interference membrane 121 is constructed to fully wrap the outer layer 115, thereby protecting the outer layer 115 from further oxidation effects. The interference membrane 121 is also constructed to substantially restrict the passage of larger molecules, such as acetaminophen, to reduce contaminants that can reach the platinum and skew results. Further, the interference membrane 121 may pass a controlled level of hydrogen peroxide ($H_2O_2$) from the enzyme membrane 122 to the platinum outer layer 115. Compositions for the interference membrane 121 and enzyme membrane 122 may be as described in U.S. patent application Ser. No. 17/449,562, entitled "Working Wire for a Continuous Biological Sensor with an Immobilization Network," and U.S. patent application Ser. No. 17/449,380, entitled "In-Vivo Glucose Specific Sensor," which are owned by the assignee of the present disclosure and incorporated herein by reference as if set forth in their entirety.

Figure 2:
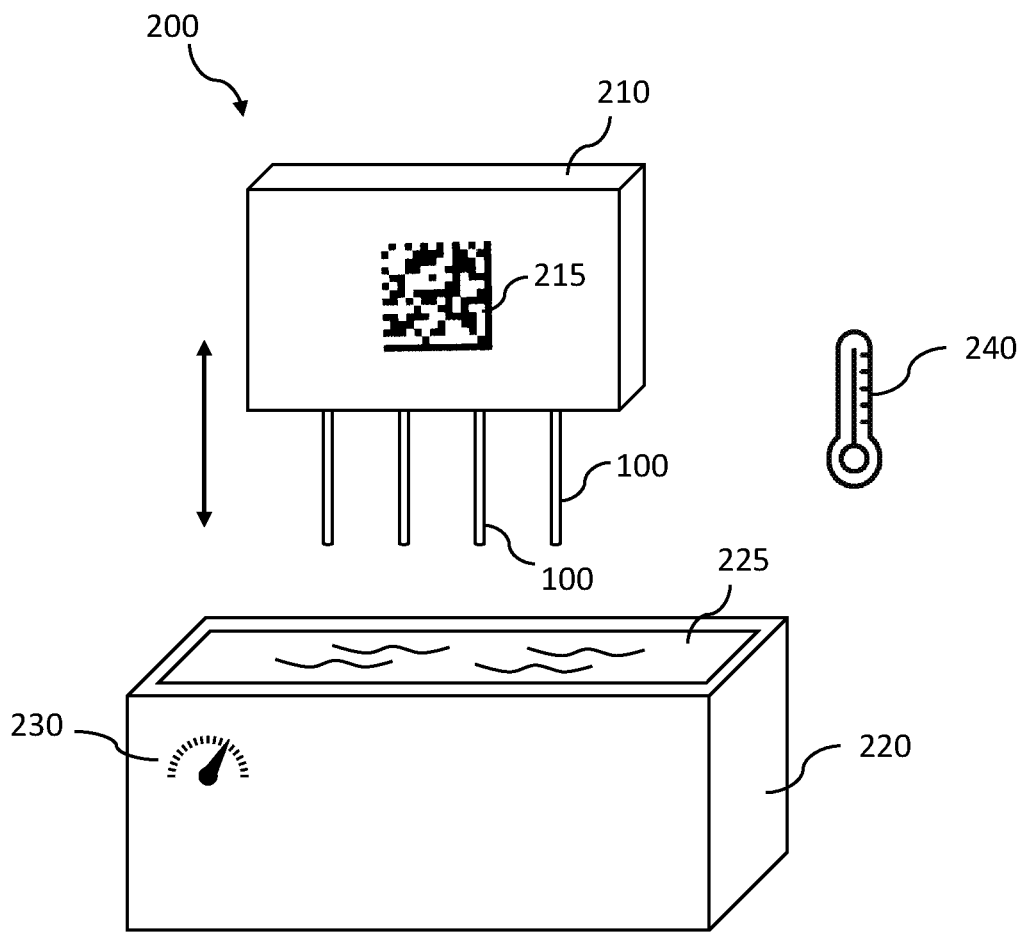
FIG. 2 is a schematic of a dipping system, in accordance with some embodiments.

FIG. 2 is an isometric view of a dipping station 200 having a fixture 210 and a tub 220, in accordance with some embodiments. Multiple working wires 100 are mounted into the fixture 210. The fixture 210 is a holder, depicted as a block in this embodiment, for transporting the working wires 100 through a dipping process during manufacturing. The fixture 210 may also be referred to as a carrier or tray. The working wires 100 may be secured into the fixture 210 by, for example, clamps, spring-loaded clips, set screws, adhesive fasteners, or other mechanisms. The fixture 210 may include an identifier such as a scannable code 215 (e.g., bar code or quick response "QR" code) for tracking the progress of the particular fixture 210 during manufacturing. Four working wires 100 are shown in this embodiment, but the fixture 210 may be configured to hold more or fewer working wires in other embodiments. The working wires 100 are mounted in a single row in this embodiment, spaced apart and extending from an edge of the fixture 210 so that each one can be measured individually from various angles. In other embodiments the wires may be arranged in other fashions such as in more than one row, aligned or staggered from each other, as long as sufficient space is between the wires to enable each wire to be measured separately.

The tub 220 holds a coating solution 225. The working wires 100 are submerged into the coating solution 225 to create a desired membrane on the wire. For example, the dipping process may be used to create interference membrane 121, enzyme membrane 122, or glucose limiting membrane 123. Each membrane may require several dips (i.e., multiple coating iterations) to build up a desired thickness of the full membrane. Using several dipped layers to create a membrane can be advantageous in reducing the occurrence of pinholes in the membrane compared to creating the entire membrane thickness with a single dip. However, multiple dips require more manufacturing time than a single dip, which increases costs. Embodiments of the present disclosure enable multi-dip processes to be performed in a cost-effective manner by minimizing the number of dips to achieve a desired final thickness of a membrane, while maintaining accurate dimensions of the membranes.

The tub 220 may include one or more sensors 230 that monitor aspects of the coating solution such as viscosity or solution temperature. The system may also include environmental sensors 240 to monitor aspects of the ambient environment such as air temperature, relative humidity and airflow velocity. Embodiments of the present disclosure beneficially utilize these environmental sensors to provide input to a controller to adjust dipping parameters during manufacturing. In this manner, adjustments are automatically made by the controller to account for process variations that are extremely difficult to control manually. For example, changes in solution properties during the manufacturing process due to environmental factors can advantageously be compensated for in real-time. Lot-to-lot variations in solution viscosity or solids content can further affect how the environmental factors affect the solution. These impacts can also be accounted for by the present systems and methods.

Figure 3A:
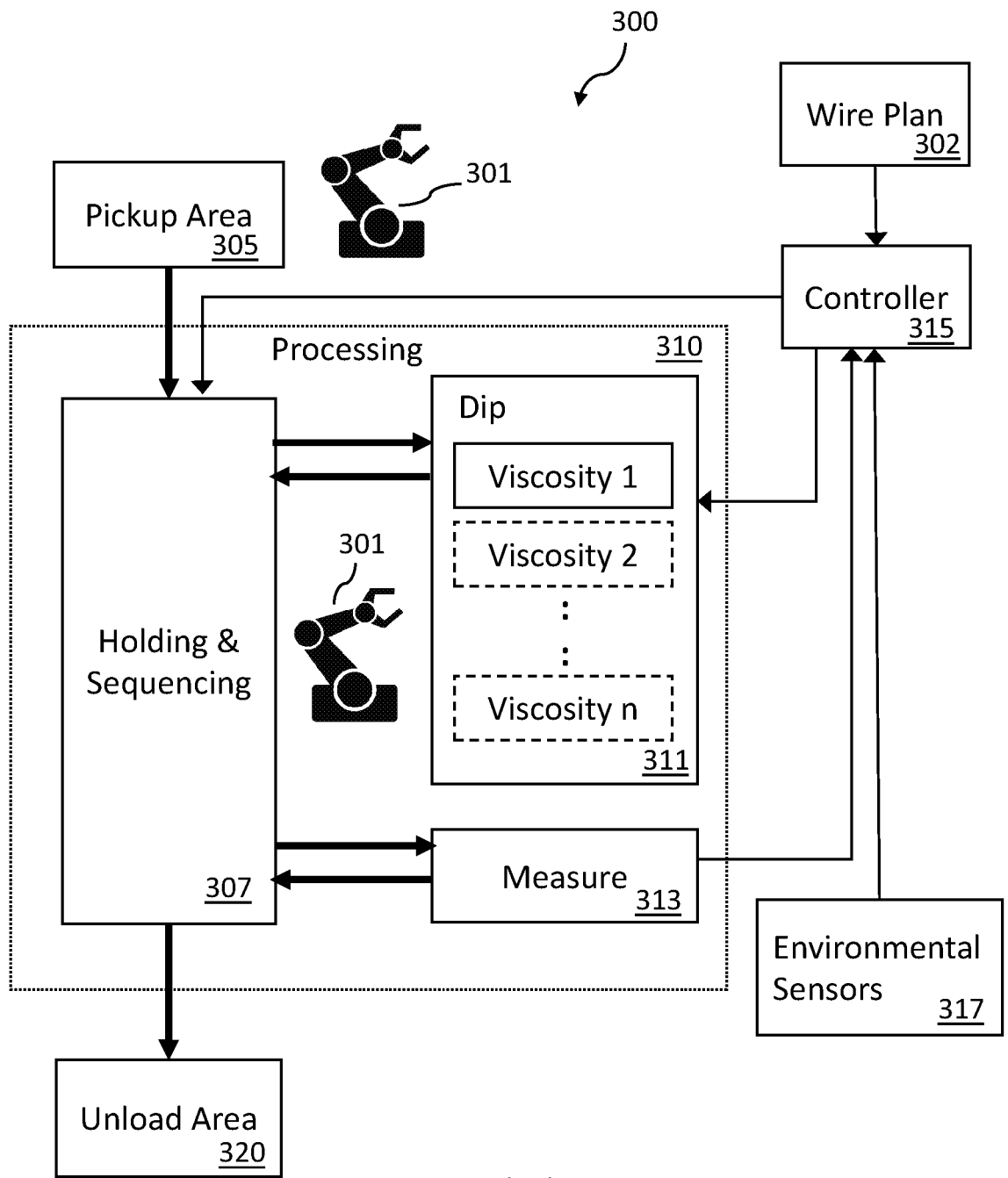
FIG. 3A is a block diagram of a system for making a working wire, in accordance with some embodiments.

FIG. 3A illustrates a block diagram of a system 300 for manufacturing working wires, in accordance with some embodiments. System 300 is automated by a controller 315 and an industrial robot 301 constructed for manufacturing purposes. An industrial robot is programmable for high-speed automated repetitive functions and provides movement in three or more axes. These industrial robots may be programmed for various functions, such as welding, painting, assembly, disassembly, pick and place, packaging, and labeling. Industrial robots are available in various configurations, such as a simple robotic arm, or a more sophisticated articulated robot. Articulating robots have rotary joints that can provide additional movement and control options. The industrial robot may be tabletop, floor mounted, or even mobile depending upon the size and sophistication of the overall manufacturing facility. In one embodiment of system 300, the industrial robot 301 is a 6-axis robot having articulated joints. It will be understood that other robots, or multiple robots may be used in some embodiments.

System 300 is part of an overall manufacturing process for creating a sensor for a continuous biological monitor, and in particular, the part of the process for manufacturing a working wire. System 300 receives work-in-progress ("WIP") working wires, mounted in fixtures 210 of FIG. 2, where the wires have some or none of the membrane layers applied. For example, when entering the system 300 for processing, the WIP working wires may only consist of a substrate as described in FIG. 1, or may have the substrate and an enzyme membrane, or may have the substrate, an enzyme membrane and an interference membrane. The system 300 may apply one or more of the enzyme membrane, the interference membrane, and/or the glucose limiting membrane, which may be efficiently and accurately applied through a dipping process.

System 300 uses one or more robots 301, such as a 6-axis robot, to collect the WIP working wires from a pickup area 305. The robot 301 processes the working wires through a processing area 310 and moves the final dipped working wires to an unloading area 320. The industrial robot that processes the wires through the processing area 310 is preprogrammed with a wire plan 302 that is stored in a controller 315. That is, the programmed software (e.g., including algorithms for controlling and adjusting dipping parameters) is written into the firmware of the robot 301. The controller 315 may be, for example, a programmable logic controller. The wire plan 302 defines the detailed requirements for the working wire. For example, the wire plan 302 may set out the specific range of thicknesses allowable for the membrane, such as the total thickness of the layers for forming a glucose limiting membrane. Further, the wire plan 302 may define the initial process steps for robotic control, which may then automatically adapt according to customized algorithms as described herein, depending upon environmental conditions and actual thickness measurements.

Figure 3B:
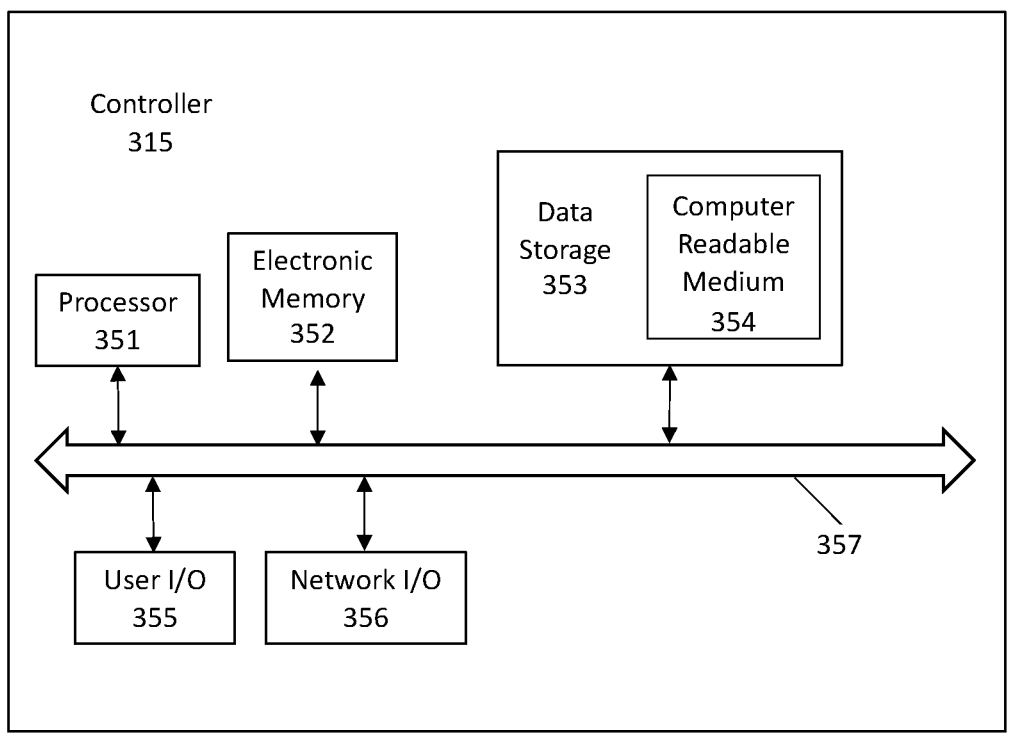
FIG. 3B is a schematic of the controller of FIG. 3A, in accordance with some embodiments.

FIG. 3B is a simplified schematic diagram showing an embodiment of controller 315 (representing any combination of one or more of controllers) for use in the system 300, in accordance with some embodiments. Other embodiments may use other components and combinations of components. For example, the controller 315 may represent one or more physical computing devices (e.g., programmable logic devices (PLCs) and/or other computer hardware processors) that include or are in communication with computer servers, such as web servers, rack-mounted computers, network storage devices, desktop computers, laptop/notebook computers, etc., depending on the complexity of the system. In some embodiments implemented at least partially in a cloud network potentially with data synchronized across multiple geolocations, the controller 315 may include one or more cloud servers. In some embodiments, the functions of the controller 315 are enabled in a single computer device. In more complex implementations, some of the functions of the computing system are distributed across multiple computing devices, whether within a single PLC, a single server farm facility or multiple physical locations.

In the illustrated embodiment, the controller 315 generally includes at least one processor 351, a main electronic memory 352, a data storage 353, a user input/output (I/O) 355, and a network I/O 356, among other components not shown for simplicity. The components are connected or coupled together by a data communication subsystem 357. A non-transitory computer readable medium 354 includes instructions that, when executed by the processor 351, cause the processor 351 to perform operations including determining thicknesses differences between target and measured values (e.g., difference between a thickness setpoint and an aggregate criteria for the plurality of diameters), and calculating adjusted parameters for the dipping process described herein.

In accordance with the description herein, the various components of the presents systems or methods generally represent appropriate hardware and software components for providing the described resources and performing the described functions. The hardware generally includes any appropriate number and combination of computing devices, network communication devices, and peripheral components connected together, including various processors, computer memory (including transitory and non-transitory media), input/output devices, user interface devices, communication adapters, communication channels, etc. The software generally includes any appropriate number and combination of conventional and specially developed software with computer-readable instructions stored by the computer memory in non-transitory computer-readable or machine-readable media and executed by the various processors to perform the functions described herein.

Layer thicknesses formed in a dipping process are dependent upon several factors. Example dipping parameters and adjustments that may be made depending on the thickness measurements and other sensor information, in accordance with embodiments of the present disclosure, include the following:

Dip solution viscosity: A thicker solution provides a thicker layer per dip than a thinner solution. The dip solution has an initial known viscosity, which may change over time depending upon temperature, mixing, and evaporation.

Dip solution temperature: A cooler solution will provide a thicker layer per dip than a warmer solution. The dip solution has an initial known temperature, which may change over time depending upon external temperature, mixing, and evaporation.

Immersion speed: Inserting the working wire into the solution at a slower rate will result in a thicker layer per dip than a faster rate. Based on all the expected parameters, an initial speed in is set, which may change for subsequent dips depending upon environmental conditions and actual thickness measurements.

Dwell time: Dwell time is the amount of time that the working wire remains fully immersed in the solution. A longer dwell time will result in a thicker layer per dip than a shorter dwell time. Based on all the expected parameters, an initial dwell time is set, which may change for subsequent dips depending upon environmental conditions and actual thickness measurements.

Withdrawal speed: Removing the working wire from the solution at a slower rate will result in a thinner layer per dip than a faster rate. Based on all the expected parameters, an initial withdrawal speed is set, which may change for subsequent dips depending upon environmental conditions and actual thickness measurements.

Airflow: Increasing airflow as the working wire comes out of coating solution lowers the solvent evaporation time and improves uniformity of the coating. Measurements of airflow velocity and/or relative humidity can be used to adjust dipping parameters.

Lot-to-lot variations in the coating solution will also affect the dipping process. For example, the viscosity of the solution for one batch used on a first day can be different from the viscosity of another batch used on a subsequent day, such as the viscosity varying ±10% from the first day. In other examples, the molecular weight or solids content can vary between batches of coating solution. Conventionally, such variations would require the parameters of the manufacturing process to be retuned manually for each batch of coating solution. Instead, in the present disclosure, adjusting or retuning of the parameters is automatically performed by the specifically designed system and algorithms, thus improving manufacturing output by reducing defects and processing time. The parameters can also be adjusted in real-time, such as during the dipping process (e.g., between dips) in addition to between batches of coating solution.

Coating processes also tend to be non-linear in nature regarding the amount of coating that is deposited with each dip, which can make the thicknesses of the dipping layers difficult to predict. Interactions of the dipping parameters with other factors such as environmental conditions are also complex. As an example of the non-linear nature of dipping processes, each dip of a coating solution may result in a different layer thickness. For instance, a first dip may result in a 1 micron thick layer, a second dip in the same solution may result in 4 microns, and a third dip may result in 12 microns. Furthermore, the layer thicknesses can be affected by the state of the object being dipped. For example, dipping an uncoated wire (e.g., core 113 of FIG. 1 with or without outer layer 115) in a coating solution may result in different layer thicknesses than a wire that already has an enzyme membrane on it, even though the two samples are dipped in the same coating solution under the same dipping conditions. The methods and systems of the present disclosure can adjust dipping parameters during the dipping process (i.e., in-line, while individual layers are being created on the working wire, prior to completion of the full membrane thickness) to compensate for these complex and often unpredictable interactions.

Using the wire plan 302 in FIG. 3A, a customized program in controller 315 is used to control the industrial robot 301 (which may include more than one robot). The robot uses its articulating arm to pick up WIP working wires from pickup area 305. The WIP working wires are previously loaded into fixtures, trays, or carriers for holding multiple wires. Such fixtures may hold, for example, 4, 8, 10, or more working wires per fixture. The robot picks up the fixture of WIP working wires and places it in a holding and sequencing area 307. Since the dipping process requires that the working wires be dipped in solution multiple times, and the working wires must be dried or cured between each dip, the holding and sequencing area 307 allows the industrial robot to be moving multiple fixtures through the process at one time. Depending on the specifics of the timing requirements, the industrial robot may be managing many fixtures, such as ten or more fixtures through the processing area 310 at one time.

The robot picks up a fixture from the holding and sequencing area 307 and moves it to the dipping station 311 (e.g., dipping station 200 of FIG. 2). The dipping station may include the same coating solution in more than one available viscosity, shown as Viscosity 1, Viscosity 2, through Viscosity "n" in FIG. 3A. For the initial dip for the fixture, the robot will perform the dip according to the wire plan 302, as instructed by controller 315. For subsequent dips in a sequence of multiple dips for the fixture, the robot will perform the dip according to the wire plan along with applying adjustments made by controller 315. In embodiments, thicknesses of the coating layers are measured as an in-line process—that is, as the working wires progress through the dipping process—and dipping parameters are adjusted as needed to achieve the required thicknesses within a target window of a thickness setpoint and/or within a predefined number of dips. For example, a total thickness of a membrane (e.g., enzyme membrane or glucose limiting membrane) may be desired to be 4 microns to 25 microns, such as 6 microns to 19 microns, where multiple coating layers are applied to form the total thickness. A target window for a desired setpoint thickness may be, for example, ±1 to ±3 microns, such as ±2 microns, of the setpoint thickness.

Limiting or reducing the number of dips required to manufacture the working wires can reduce costs by enabling more working wires to be manufactured in a certain amount of time. Monitoring the layer thicknesses while the wires are being produced can also reduce costs by producing less defects and can also improve the accuracy of the produced wires, thus improving quality. Conventional techniques typically use a fixed withdrawal speed and preset number of dips. After all the dips have been completed, the wires are measured and those that do not pass are rejected. In contrast, the present systems and methods measure the wires in-process; that is, after each dip. By using layer thickness measurements as feedback, dipping parameters can automatically be adjusted before the next dip is performed, to enable the working wire to be completed accurately, without impacting the processing time. For example, if the coating layers of the membrane are found to be thinner than expected, the dipping parameters can be adjusted to create thicker layers on the next dip so that the total thickness of the membrane can be met without adding more dips than originally planned. In another example, if the coating layers are found to be closer to the final desired thickness than expected, the dipping parameters can be adjusted to create a thinner layer on the next dip to avoid overshooting the diameter specification, which could result in a rejected part. Because interactions between dipping variables (e.g., environmental conditions, solution viscosity, immersion and withdrawal speeds, batch variations) are very complex in nature, and the tolerances of the layer thicknesses require extremely tight tolerances (e.g., within microns), the control and adjustments to achieve the accuracy needed are extremely difficult to perform manually or with conventional techniques. The systems and methods of the present disclosure provide control of layer dimensions and adjustment of dipping parameters that are unable to be achieved with conventional techniques.

The adjustments made by the controller 315 are based on actual thickness measurements of the working wires on the fixture. The measurements are taken by automated measurement system 313, where every working wire can be measured and at multiple locations and from different circumferential angles. The adjustments may also use information on the surrounding environment and of the dipping bath. The system 300 may have environmental sensors 317 for sensing, for example, environmental humidity, ambient temperature, air pressure, airflow, and/or ambient light. Based on the actual environment, the controller 315 may adjust the wire plan 302 to accommodate for differences between the actual environment and the expected environment of the original wire plan 302.

In making the dip, the industrial robot sets an immersion speed, a dipping depth, a dwell time, and a withdrawal speed. After the wires in the fixture have been dipped, the robot moves the fixture back to the holding and sequencing area 307. Here, the working wires in the fixture dry and cure. The robot may then pick up another fixture to dip, or in some cases may pick up a fixture that has been previously dipped, dried and cured.

For working wires that have already been dipped and cured, the industrial robot moves the fixture to automated measurement system 313, where the diameter of each wire is measured using an in-line optical measurement tool (i.e., optical measurement tool used during the manufacturing process) to derive a coating thickness that has accumulated from the last dipping cycle. The optical measurement tool may be, for example, an optical micrometer that utilizes a laser beam to measure dimensions in a non-contact manner. The micrometer detects the size of the working wire by measuring the shadow of the object that is within the path of the laser beam. Because the robot is adjustable on multiple axes and can be very precisely controlled, each working wire in the fixture may have its thickness measured along its entire length and at different angles around its entire circumference. In this way, thickness is measured for every working wire at each dip for multiple lengthwise positions and angular rotations. In some embodiments, measurements can be made at more than one location along a length of a wire, and then the fixture can be rotated around a longitudinal axis of the wires so that the diameters are measured again along their length from a different orientation. In an example embodiment, each wire can be measured at 10 to 40 points along its length, and from three different angles at each point. Once measured, the industrial robot moves that fixture back to the holding and sequencing area 307, or if the working wires now meet the specification of the wire plan 302, then that fixture may be moved to the unloading area 320. If a fixture is found to have too many wires that are out of specification (e.g., two of four wires in the fixture), then that fixture may be removed from the manufacturing process.

Since dip parameters are monitored for each dip of the fixture, and the precise thickness of every working wire on that fixture is measured, controller 315 may use this information to adjust the parameters for the next dip. Further, the control system may set alerts or alarms to notify an operator that assistance is needed, such as adding more solution, or some manual intervention into the process. In another example, controller 315 may be able to control certain conditions of the dipping process, such as turning on or changing the speed of a mixer within the solution, changing a heating or cooling element for the solution, or adding additional solution into the dipping container. In another example, controller 315 may adjust an environmental control, such as adjusting heating, cooling, or airflow in the manufacturing area.

The measurement process using the robot has a precision that may enable variations in thickness to be found between working wires within a fixture, such as a variation between working wires toward the right of the fixture compared to those toward the left of the fixture. This variation can be due to, for example, the coating solution having an uneven temperature or an uneven viscosity. The controller 315 can be aware of these uneven distributions in the coating solution based on sensor information, and it can then instruct the fixture to be rotated prior to dipping, to make for a more even dip among all the wires. In this way, system 300 provides closed-loop control to precisely build the overall membrane to the desired thickness. The controller 315 can adjust dipping parameters based on an overall target thickness, such as an average or a median, as an aggregate criteria for the plurality of working wires in a fixture, where the overall target thickness is within a target window of the thickness setpoint. The measured aggregate criteria used for the plurality of working wires in the fixture may be a measured value such as one or more of a mean, a median, and/or a coefficient of variance. In some embodiments, the aggregate criteria may comprise all three quantities of a mean, a median, and a coefficient of variance of the measured diameters to determine what adjustments to make in the dipping parameters. In some embodiments, the thickness difference between a measured thickness and a setpoint thickness is determined using a variance of the plurality of diameters of the working wires in a fixture. The variance may be a lengthwise variance in an individual coated wire of the fixture and/or a rotational variance in an individual coated wire in the at least two coated wires. In other embodiments, the variance comprises a difference in diameters between two coated wires in a fixture, where the first coated wire and the second coated wire are mounted on different sides of the fixture from each other. From analyzing the variance within a single wire and/or between different wires, a uniform coating for all the wires in the fixture can be achieved.

By adjusting each dip according to a prior coating thickness measurement, the system 300 not only is able to very precisely manufacture the working wires, but throughput can be maximized. As will be appreciated, manufacturing throughput may be increased by reducing the number of dips. In some embodiments, at least three dips are required for each fixture, with possibly up to ten dips. In some embodiments, controller 315 may be programmed to optimize dipping parameters to reduce the number of dips, or at least assure that a proper thickness is achieved in the predefined number of dips. For example, if controller 315 is preset for five dips, but actual measurements show that the desired thickness can be achieved in four dips, then the industrial robot has increased manufacturing throughput by 20%. In some embodiments, the controller 315 strives to minimize the number of dips to achieve a thickness setpoint within a target window. In some embodiments, the controller 315 strives to achieve an overall target thickness within a target window of a thickness setpoint, using not more than a maximum number of dips. Calculating adjusted parameters for the dipping process may include reducing a total number of dips from a predefined number of dips to achieve a desired coating thickness.

In some embodiments, multiple coating solutions with different viscosities may be provided (e.g., as shown for dipping station 311 of FIG. 3A) to enable further improvement in thickness control. For example, two or more viscosities of the same coating solution can be available in separate tubs. Controller 315 can utilize thickness measurements and environmental information to calculate whether a thinner or thicker viscosity solution can more accurately or quickly achieve the desired thickness than the viscosity that is currently being used. The controller 315 can then instruct the industrial robot 301 to use the tub of the needed viscosity. For example, if an additional 0.002" in coating thickness is needed but the previously used coating solution is predicted to add 0.0015" in thickness, the controller may decide to switch to a higher viscosity solution that is able to achieve the 0.002" in one dip rather than using the previous coating solution which would require more than one dip or would not achieve the desired thickness as accurately. In embodiments, a coating solution of a dipping process has a first viscosity, and an additional coating solution has a second viscosity, where the second viscosity is different from the first viscosity. Calculating the adjusted parameters for the dipping process may include choosing the coating solution or the additional coating solution.

In embodiments, a system for a coating working wire for a continuous biological sensor includes one or more robots 301 for transporting a fixture 210, the fixture being configured to hold a plurality of wires 100. The wires are mounted in the fixture with spacing between the wires and extending from an edge of the fixture such that each wire can be measured individually, along their length at multiple locations and from different rotational angles. The robot may have an articulating arm or other mechanism for picking up and placing the fixture at various stations in a dipping manufacturing process. The stations may include a pickup area 305, a holding station (e.g., holding and sequencing area 307), a dipping station 311, a measurement station 313, and an unloading area 320. A single robot may be used to transport the fixture between all of the stations, or multiple robots may be positioned in the manufacturing area to move the fixture to the different stations. In some embodiments, a fixture can be moved between one or more of the stations manually. A controller 315 is in communication with the robot 301 and comprises algorithms and instructions for adjusting dipping parameters for the dipping station or holding station (e.g., for drying time). The controller 315 may be separate from or contained in the robot 301, and may be in communication with other computing devices such as hardware processors and/or cloud servers. Environmental sensors 317 may provide input to the controller, where the environmental sensors 317 can be, for example, an ambient temperature sensor, an ambient humidity sensor, an ambient air flow sensor, a temperature sensor for the dipping station, a viscosity sensor for a coating solution in the dipping station, or other sensors described throughout this disclosure.

The measurement station 313 has a non-contact measuring tool such as an optical micrometer, optical profile measurement system, optical coordinate measuring machine (CMM), or other optical scanner/tracker. Measurements of wire diameters are taken after each dip to derive coating layer thicknesses, where multiple dips may be required to complete the full desired thickness of the membrane for the working wire. The robot positions the fixture holding the plurality of wires such that the measuring tool can take measurements, such as diameters, along the length of each wire. The robot then rotates the fixture (i.e., changes the angle of the fixture relative to the measurement instrument) so that the diameter measurements can be repeated along the length of each wire from a different angle (i.e., orientation). The controller synthesizes all the measurements for the plurality of wires on the fixture into an aggregate criteria or value to determine a difference in thickness between a thickness setpoint and the aggregate criteria/value. The controller then calculates adjusted parameters for the dipping process based on the difference in thickness, using relationships between parameters that are stored in the controller.

Figure 4A:
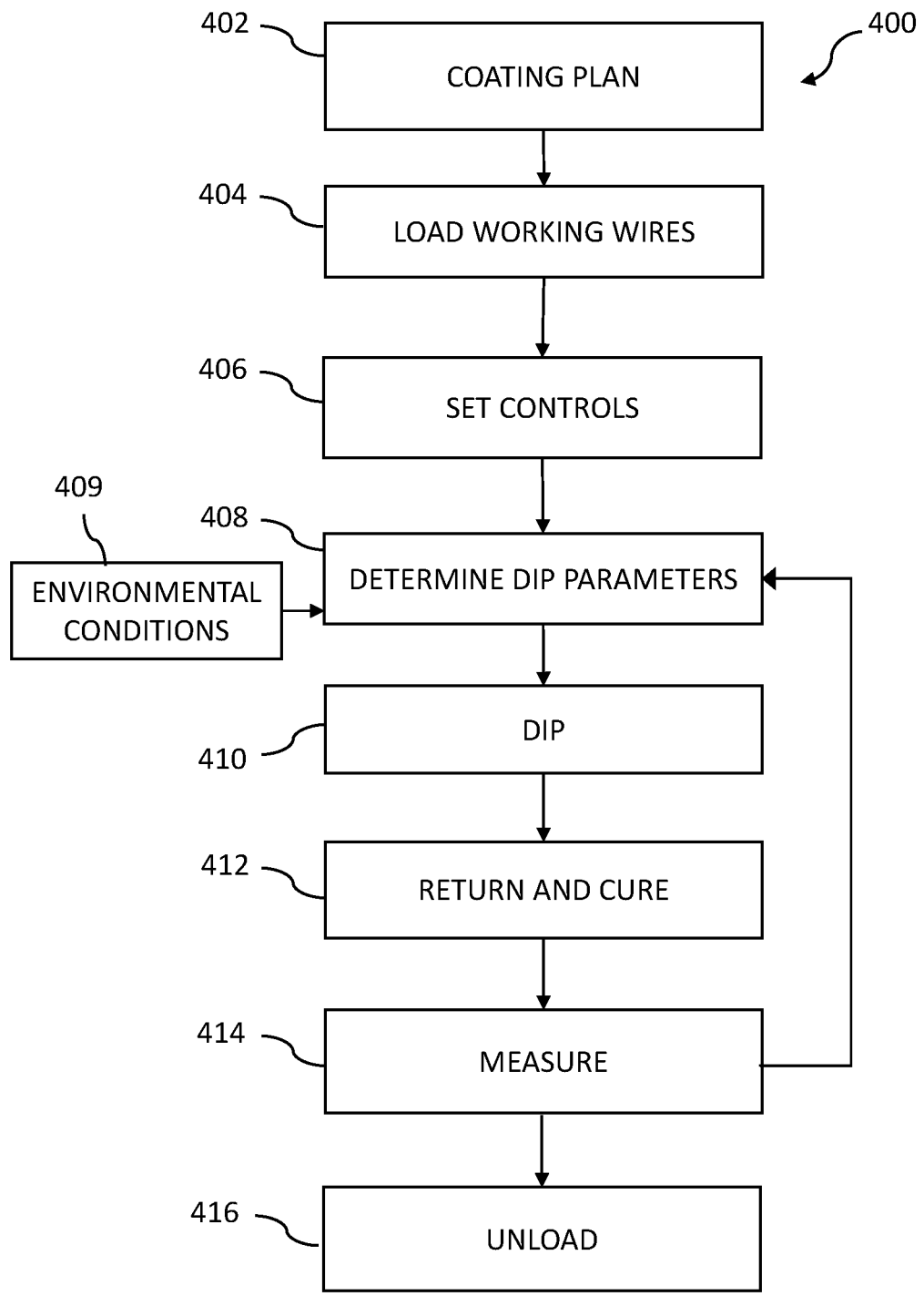
FIG. 4A is a flowchart of a process for making a working wire, in accordance with some embodiments.

Referring now to FIG. 4A, a flowchart is illustrated representing a method 400 for applying coatings to a working wire for a continuous biological monitor. Method 400 uses an automated system 300 as described with reference to FIG. 3A. In method 400, a coating plan is initially set in block 402. This coating plan sets an acceptable range of thicknesses for the membrane being created on the working wire. The coating plan may also have a predefined target number of dips, which may be, for example, between 3 and 10. It will be understood that the number of dips may be selected due to application-specific requirements. It will also be understood that the number of dips may be adjusted by the adaptive nature of method 400, and that it is desirable for throughput purposes to have a fewer number of dips. The coating plan in block 402 also defines the parameters for the dipping solution, such as an initial solution viscosity, solution temperature, immersion speed, dwell time, and withdrawal speed. The coating plan also may be initially set according to expected environmental conditions such as ambient temperature, humidity, and airflow. The coating plan of block 402 is used to program the industrial computer, which may be in the form of a controller in communication with a robot being used to perform the dipping process.

Block 404 involves providing a plurality of wires in a fixture. Each of the individual fixtures, carriers, or trays is loaded in block 404 with a set of WIP working wires, for example four or more wires. The fixture holding the set of WIP working wires is placed in a holding area so that the industrial robot may load it for dipping. This holding area may be, for example, an open area, a carousel, conveyor belt, a platform, or a moving robotic platform. It will also be understood that the industrial robot may be a mobile industrial robot that may move to another area of the manufacturing facility to load the fixture or carrier.

Method 400 then sets controls in block 406 for the overall process. For example, the dipping solution may be in a container with a mixing mechanism, such as a mixing blade, and the controls may include a mixing speed. In another example, the dipping station may have a heating plate for increasing or decreasing the temperature of the dipping solution, and the controls may set a temperature for the solution. The method 400 may control the mixer and heating plate to assure even coating and maintain proper viscosity of the coating solution. In block 408, the dipping parameters are determined. For the first dip of a working wire, the dipping parameters are set according to the initial coating plan, with some embodiments also taking into account current environmental conditions 409. Further, the initial dipping parameters may be adjusted due to the actual operation of method 400 on prior WIP working wires, where data on previously dipped working wires may be stored and analyzed in, for example a cloud server. For example, if prior working wires have required longer dipping to create the desired target thickness, then the initial dip may be adjusted to account for the known and measured current operation of the system. As described above, the dipping parameters include immersion speed, depth of insertion, dwell time, and withdrawal speed; other parameters may also be adjusted.

With the parameters set, the industrial robot then dips the fixture or carrier into the dipping solution as shown in block 410. After dipping the plurality of wires into a coating solution according to the parameters for the dipping process, the industrial robot returns the fixture or carrier to the holding area for drying and curing as shown in block 412. While the working wires in the fixture are drying and curing, the industrial robot will proceed to work on other fixtures or carriers, for example dipping them, or measuring them.

After sufficient time has elapsed for the wires that were returned in block 412 to dry, the industrial robot will then pick up that fixture and move it to a measurement system (e.g., automated measurement system 313 of FIG. 3A) in block 414 to determine the thickness of the coating layer. The measuring of block 414 is performed as an in-line process, during the manufacturing flow of the method 400. The measuring involves using an automated measurement system to measure a plurality of diameters in three dimensions as described throughout the specification, along a length of at least two coated wires of the plurality of wires in the fixture. In some embodiments, measurements of the working wires may be taken before the method 400 begins, such as to establish the wire diameters with any membrane layers that were previously applied. These baseline diameters (i.e., diameters prior to beginning the dipping process with the current coating composition) can be input into the controller to set controls (block 406) and dipping parameters (block 408) as needed.

Figure 4B:
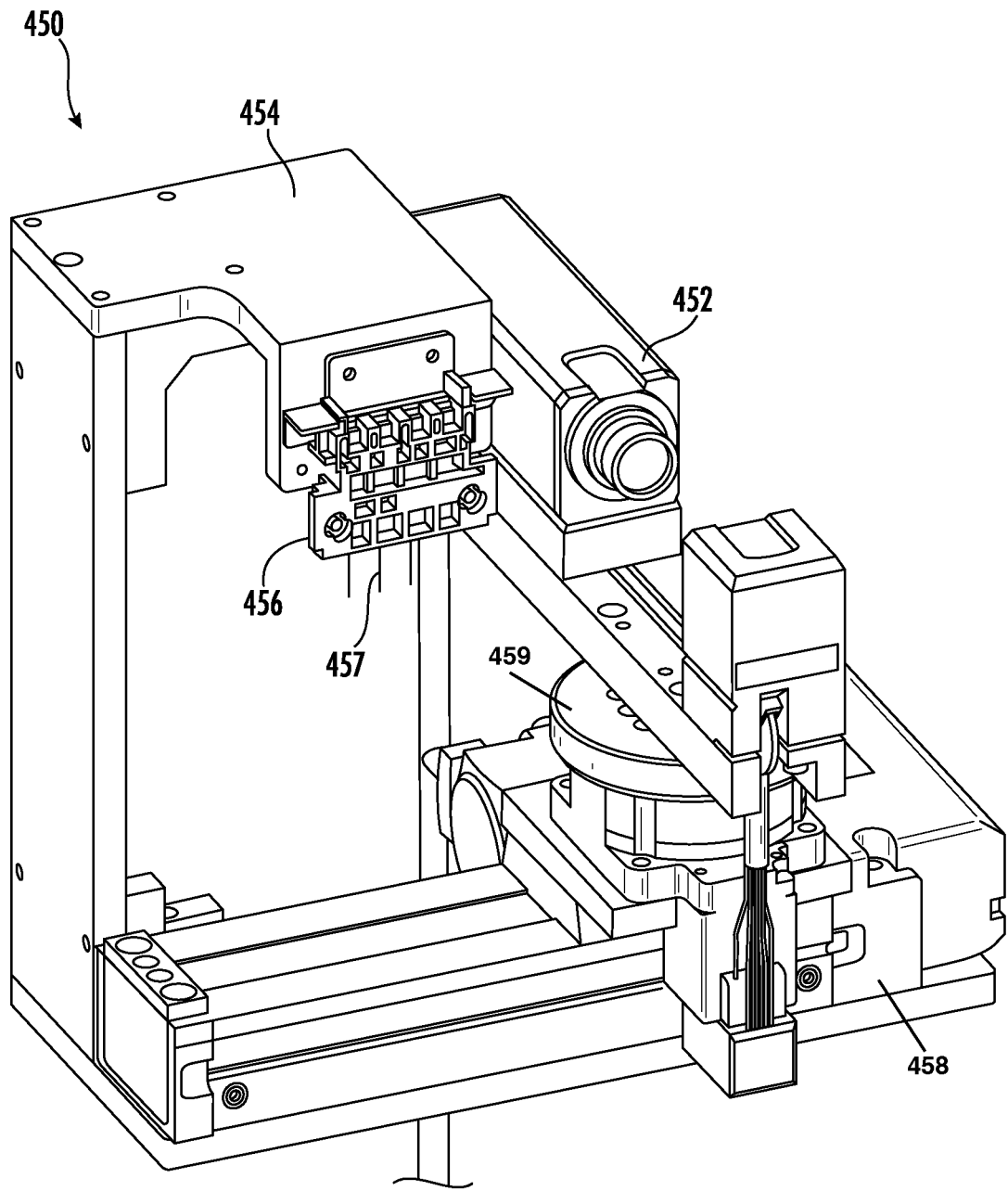
FIG. 4B is an isometric view of an automated measurement station, in accordance with some embodiments.

FIG. 4B is an isometric view of an automated measurement system 450, in accordance with some embodiments. Automated measurement system 450 includes measuring equipment 452, such as an optical scanner or laser measuring station, and a fixture holder 454 for temporarily storing one or more fixtures 456 having working wires 457. In the embodiment shown, the optical measurement tool (measuring equipment 452) is mounted on a stage that has both a linear actuator 458 and a rotational actuator 459, which enables the optical measurement tool to be moved so that it can measure the wires on the fixture from various angles and at various points along the length of the working wires. In another embodiment, the fixture 456 can be carried by a robotic arm to the measuring equipment 452 to be measured at various points along the working wires and from different angles, as described above.

Returning to FIG. 4A, the measuring station in block 414 may measure the overall diameter of the wire and derive the thickness of the most recent layer that was created, based on the original uncoated wire diameter and any previous coating measurements. Embodiments involve determining, by a controller that is in communication with the automated measurement system, a thickness difference. The thickness difference is a difference between a thickness setpoint and an aggregate criteria for the plurality of diameters. With the precise control of the industrial robot, thickness can be measured both linearly along a wire and around the circumference of each working wire. With this detailed information, the controller in method 400 can then determine the dipping parameters for the next dip as shown in the loop back to block 408. Determining of the dip parameters in block 408, after measurements have been taken in block 414, include calculating, by the controller, adjusted parameters for the dipping process based on the thickness difference. Dependent upon the workload on the industrial robot, the industrial robot may move the measured fixture directly to the dipping station and perform the next dip, or alternatively the industrial robot may return the fixture to the holding area and perform the next dip at a later time.

Because of the detailed information that is obtained on thickness for each wire, variations may be found left to right across the fixture, or top to bottom on working wires. Based on this information, the adjusted dipping parameters may comprise changing an orientation of the fixture during the dipping, compared to a previous coating iteration. For example, the industrial robot may adjust the dip by rotating the fixture 1800 for the next dip, to have more uniformity left to right. Further, uniformity may be increased by temporarily increasing the mixing speed of the coating solution so that the mixture is more evenly dispersed in the dipping container. The method may also account for the effect of increasing mixing which may also increase the rate of evaporation, thereby affecting viscosity.

When measurements of the working wires indicate that the wires have achieved the desired total membrane thickness, within an acceptable target window, the working wires are unloaded in block 416.

Figure 5:
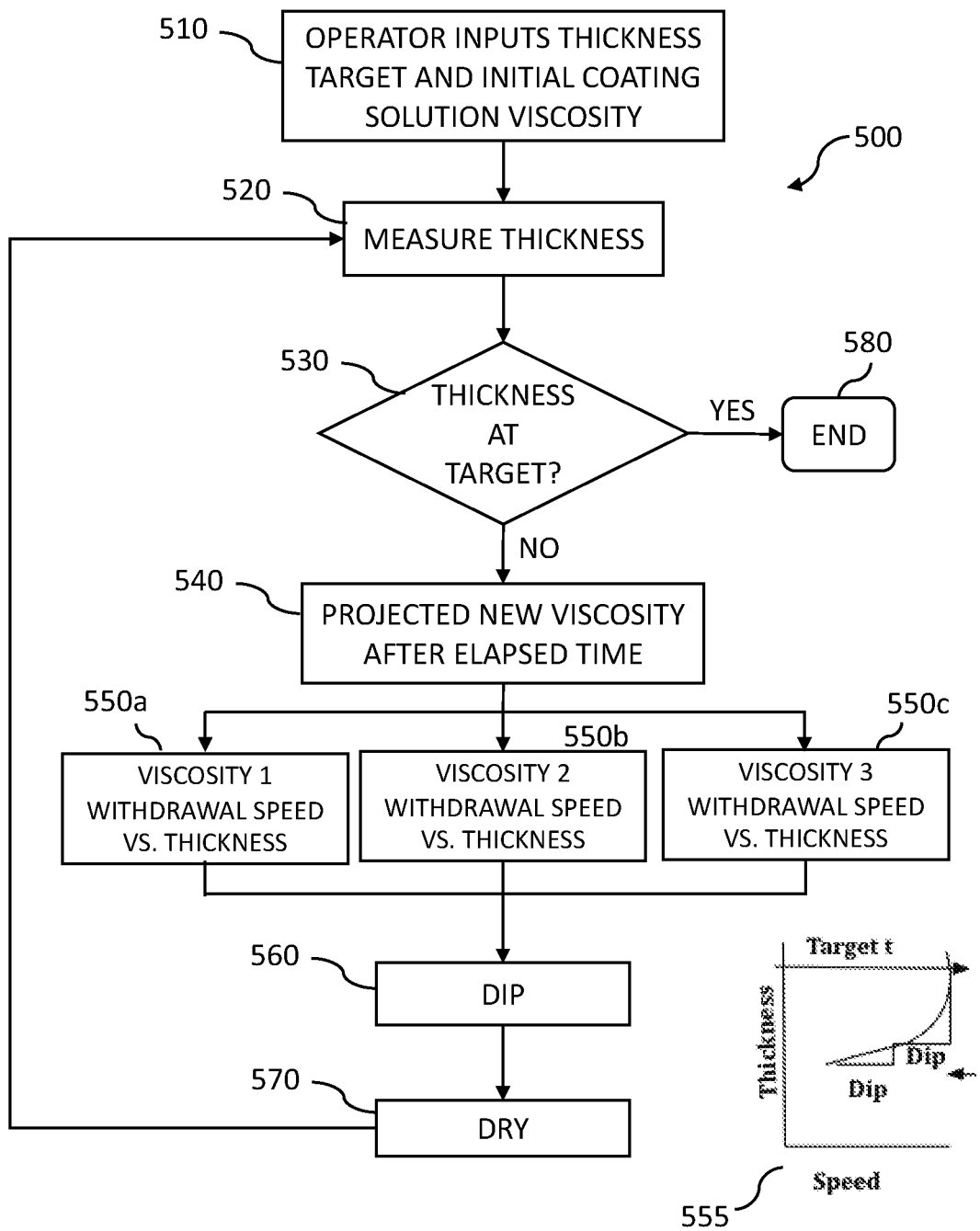
FIG. 5 is a flowchart of an algorithm for adjusting dipping parameters, in accordance with some embodiments.

The controller uses customized algorithms that uniquely adjusts dipping parameters based on information acquired during the dipping process such as coating thicknesses, coating solution viscosity and temperature, ambient temperature, and airflow velocity. FIG. 5 shows a flowchart representing methods 500 implemented in algorithms according to embodiments of the present disclosure. In block 510 an operator inputs a thickness target for the membrane being built and an initial viscosity of the coating solution. In block 520, the thickness of the dipped layer(s) is measured as described in relation to FIGS. 4A and 4B. The thickness used in block 520 can represent the multiple measurements taken along the lengths and around the circumferences of all the working wires on the fixture. For example, the thickness in block 520 may be an aggregate criteria involving an average and/or a median of all the measurements and may include variances within a wire or among wires of a fixture.

Following the measurement of thickness in block 520, the algorithm compares that measurement (e.g., per the aggregate criteria) to a thickness setpoint and determines the difference in block 530. If the total thickness of the working wire is within an acceptable range of the target dimension, the process is completed at block 580. If the target thickness has not been achieved, the algorithm then decides whether to alter one or more dipping parameters. In the illustrated embodiment, the algorithm alters the withdrawal speed based upon the remaining thickness that needs to be achieved and based upon a viscosity of the coating solution. Since viscosity can change during the process due to solvent evaporation, an in-line viscometer can be used to measure the viscosity, or a fixed time versus solvent loss relationship may be used to estimate the new viscosity. For example, the algorithm may optionally project a new viscosity of the solution in block 540 according to an amount of time that has elapsed since the initial viscosity was input in block 510. The new viscosity may account for environmental conditions (e.g., from environmental sensors 317 of FIG. 3A). In this manner, the algorithm can shift the withdrawal vs. thickness curves used based upon viscosity.

In blocks 550a, 550b and 550c, the algorithm chooses a withdrawal speed utilizing a series of withdrawal speeds versus thickness curves, illustrated by curve 555, that are created for ranges of potential viscosities. The range of viscosities may represent changing values of the viscosity of the coating solution over time, and/or may represent separate tubs of coating solutions with different viscosities that are available for the dipping process. Although three viscosities are shown in FIG. 5, fewer or more viscosities can be considered by the algorithm such as two to ten or more. Furthermore, although the relationships between withdrawal speed and thickness are shown as curves, the algorithm can use other forms of correlations such as a mathematical equation or a data table. The algorithm determines the optimum withdrawal speed to hit the setpoint target thickness in the fewest number of dip cycles without creating an overshoot of thickness. The algorithm also compares all values across the fixture (e.g., 4 wires) to determine the best overall thickness for the fixture within the target thickness window.

After the withdrawal speed is chosen from blocks 550a, 550b and 550c, the working wires are dipped in block 560 according to the viscosity and withdrawal speed determined by the algorithm. The working wires are allowed to dry in block 570, and then the thicknesses are measured again in block 520. The cycle between block 520 to block 570 is repeated until the target thickness is achieved.

Embodiments include adjusting parameters based on aspects other than or in addition to withdrawal speed, viscosity and thickness as described herein. In some embodiments, methods include dipping the plurality of wires using the adjusted parameters based on the thickness difference. In some embodiments, calculating the adjusted parameters is further based on environmental factors, where the environmental factors comprise, for example, an airflow and a relative humidity of the airflow. In some embodiments, calculating the adjusted parameters comprises referring to a set of correlations. Each correlation in the set of correlations may involve, for example, layer thickness as a function of withdrawal speed for a given viscosity of the coating solution. Some embodiments include determining the viscosity of the coating solution and choosing a correlation in the set of correlations based on the viscosity. Determining the viscosity may include measuring the viscosity of the coating solution or estimating a viscosity of the coating solution based on a relationship of solvent loss over time for the coating solution.

Figure 6A:
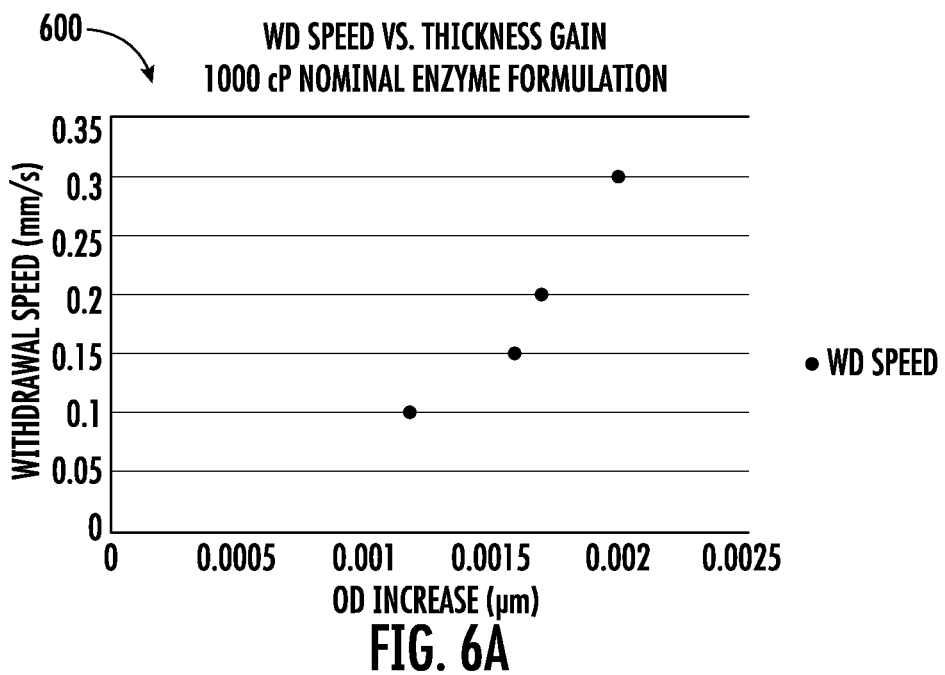
FIGS. 6A-6B are graphs of withdrawal speed versus thickness increase or diameter, in accordance with some embodiments.
Figure 6B:
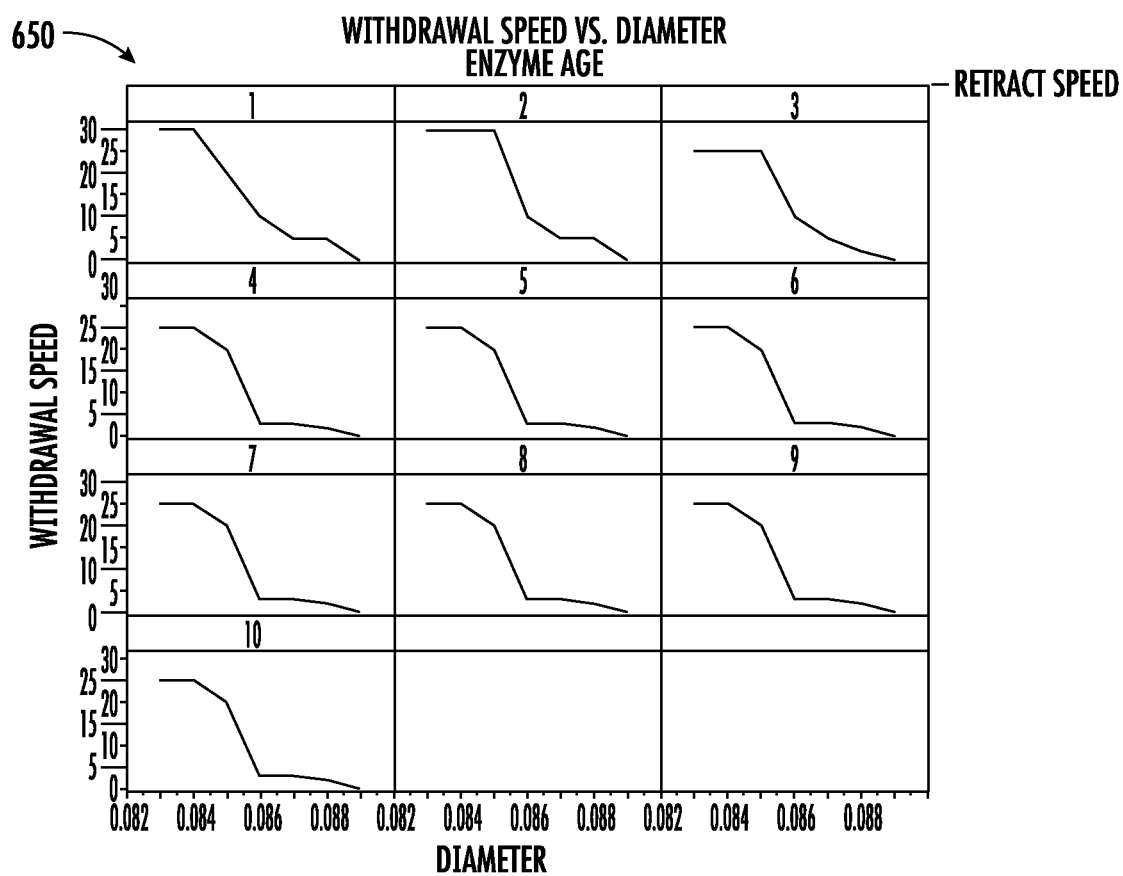

FIGS. 6A-6B show example correlations for withdrawal speed versus thickness used by heuristic algorithms for the controller, in accordance with embodiments. FIG. 6A is a plot 600 of withdrawal speed in millimeters per second as a function of the increase in thickness desired (outer diameter "OD" increase, in μm). The plot of FIG. 6A is for an enzyme formulation having a viscosity of 1000 centipoise, and shows that the higher the withdrawal speed, the greater the increase in diameter. FIG. 6A also illustrates that the relationships between withdrawal speed and diameter can be non-linear and thus difficult to compensate for manually. FIG. 6B shows a series 650 of correlations of withdrawal speed as a function of diameter, where the correlations show the change in behavior of the enzyme coating solution over time (labeled as "enzyme age"). That is, as the viscosity of the enzyme solution changes over time, such as due to solvent evaporation, the effect of withdrawal speed on diameter changes. A set of correlations can be stored in the controller for different types of solutions, such as for the interference layer, enzyme layer, and glucose limiting layer of a continuous biological monitor for glucose.

Figure 7A:
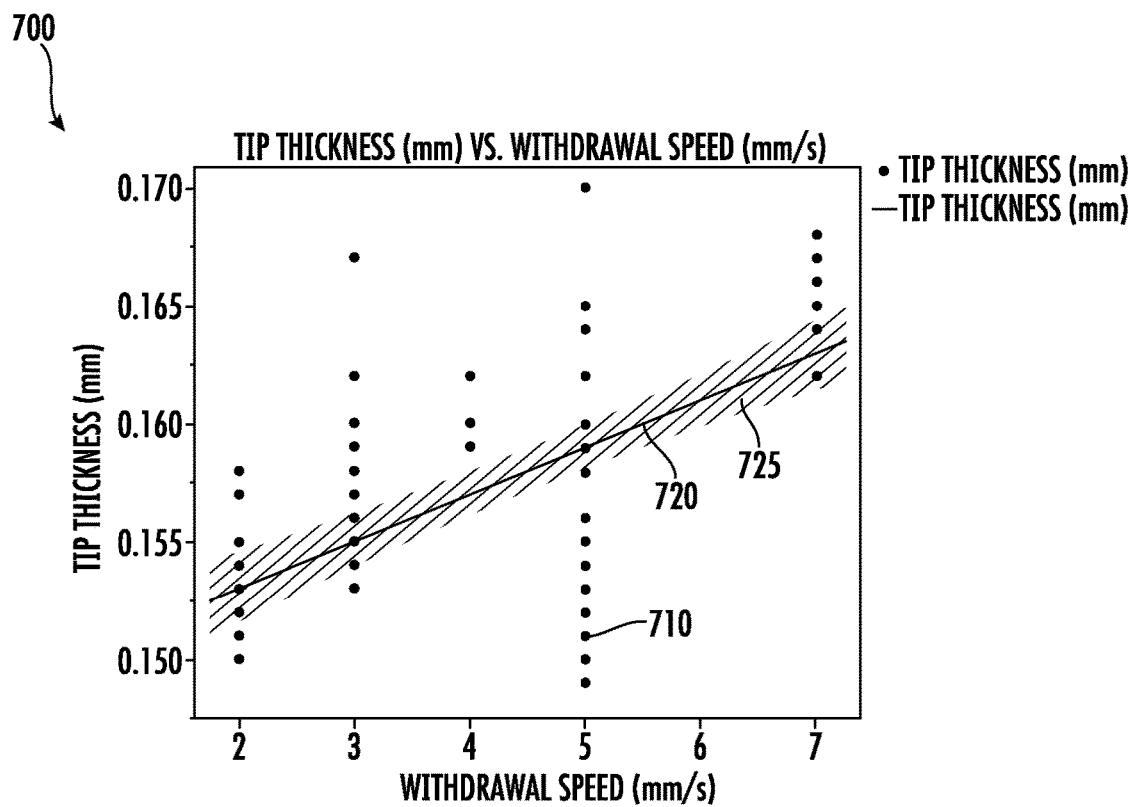
FIGS. 7A-7B are graphs of tip thickness as a function of withdrawal speed and viscosity, respectively, in accordance with some embodiments.
Figure 7B:
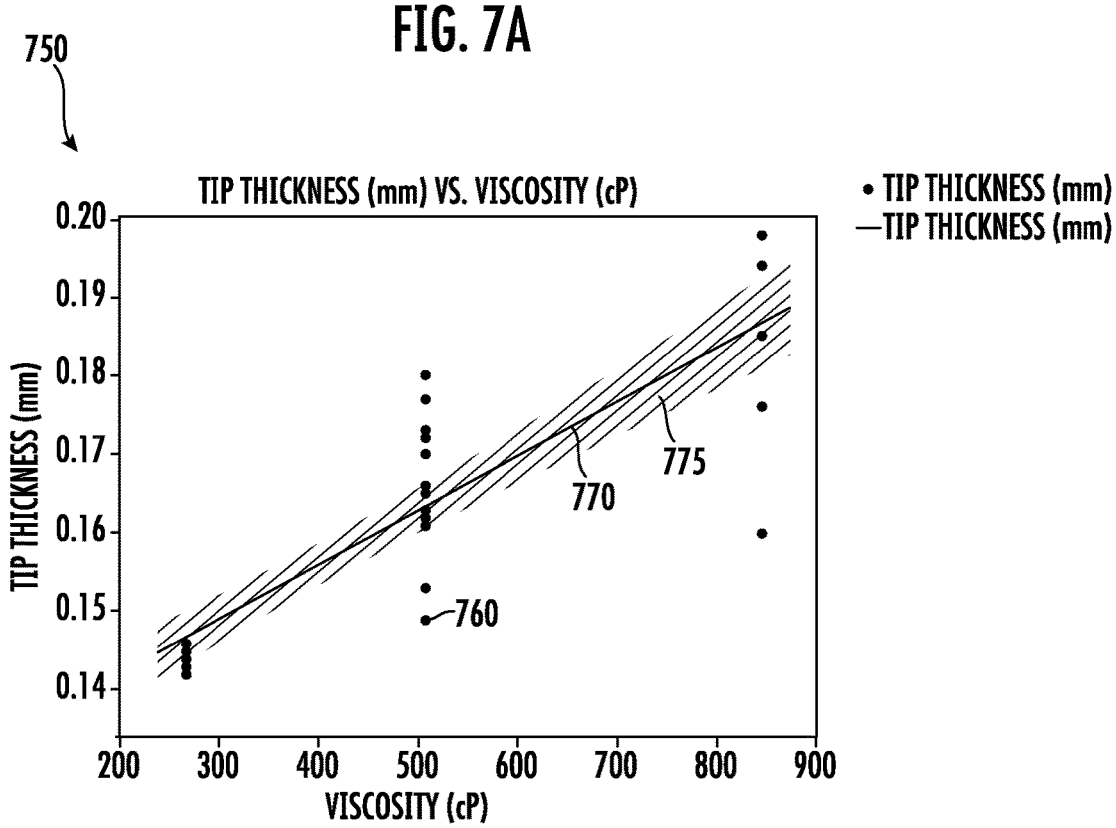

FIGS. 7A-7B show further examples of correlation data that may be used by the controller of the present disclosure for adjusting dipping parameters. The examples of FIGS. 7A-7B represent data for coating a glucose limiting membrane on wires that already had an interference membrane and enzyme membrane deposited on the wires. The figures show tip thickness in millimeters on the Y-axis, where the tip thickness is the full outer diameter (OD), including the core wire, interference membrane, enzyme membrane and in-process glucose limiting membrane.

Graph 700 of FIG. 7A shows the impact of withdrawal speed on tip thickness, where each dot is a data point 710 representing the nominal (e.g., average) OD of one wire after one glucose limiting membrane (GLM) dip. Withdrawal speeds of 2 to 7 mm/sec were utilized in this graph for a fixed viscosity. The variability in layer thickness for a given speed (i.e., data points in each column) can be due to both actual differences in thickness as well as some error in measurement by the instrument at this scale (e.g., at these micron-level dimensions, movement of the wire during measurement can affect the measured values). FIG. 7A shows that generally, the faster the withdrawal speed, the greater the resulting GLM layer thickness that is deposited. A correlation curve 720 with a standard deviation range 725, which can be calculated by the controller of the present disclosure, is superimposed on the graph 700. The correlation curve 720 shows an approximately linear relationship between thickness and withdrawal speed for the range of speeds shown. A non-linear correlation may be present over a wider range of speeds (e.g., at higher withdrawal speeds). In some embodiments, the controller may choose to use withdrawal speeds that are in this linear range during a manufacturing process. Using ranges that have linear correlations can simplify calculations for adjusting dipping parameters, particularly when several interactions must be considered by the algorithms of the controller simultaneously (e.g., viscosity, withdrawal speed, relative humidity, previous wire thicknesses, and other factors described herein).

Graph 750 of FIG. 7B is similar to FIG. 7A but showing the effect of solution coating viscosity on tip thickness. Each dot is a data point 760 representing the nominal (e.g., average) OD of one wire after one GLM dip. Three viscosities were used, with approximate values of 250 centipoise (cP), 500 cP and 850 cP for a fixed withdrawal speed. The graph 750 shows that the greater the viscosity, the greater the resulting GLM layer thickness that is created by one dip. The relationship between viscosity and tip thickness is estimated by the correlation curve 770 with a standard deviation range 775. Both graphs 700 and 750 are examples of correlations that may be part of a set of correlations that are used for calculating or determining adjusted parameters for the dipping process. For example, graph 700 is a correlation in the set of correlations comprising layer thickness as a function of withdrawal speed for a given viscosity of the coating solution. Graph 750 is a correlation in the set of correlations comprising layer thickness as a function of viscosity of the coating solution for a given withdrawal speed.

The methods and systems of the present disclosure use correlations such as those shown in FIGS. 6A-6B and 7A-7B to adjust withdrawal speeds as the viscosity changes, to beneficially achieve greater accuracy in the coating layer thicknesses built on the working wires, and/or to more efficiently achieve required coating thicknesses in fewer dips, thus reducing cost. The correlations can be obtained empirically, theoretically, or a combination thereof, and then stored in the controller. Correlations of factors involved in the dipping process, such as between withdrawal speed and coating thickness, and the evolution of solution viscosity over time, are often non-linear and not straightforward to derive. These factors are very sensitive to environmental conditions, are constantly evolving and need to be adjusted for. For example, if the viscosity of the coating solution is detected to be changing over time due to solvent evaporation or because a new lot of coating solution has been supplied, the controller can use the correlation curves to adjust the withdrawal speed for the current viscosity, to achieve a desired layer thickness based on the measurements taken for the WIP working wire. The methods and systems of the present disclosure improve quality and efficiency by monitoring and adjusting for changing conditions of the dipping process in real-time.

Although relationships between viscosity and withdrawal speed have been described for controlling the dipping process, other parameters as described herein can also be used for adjusting dipping parameters. For example, relationships between the coating solution (viscosity, temperature, mixing speed) and other parameters such as immersion speed and dwell time can be utilized. Curves similar to those in FIGS. 6A-6B and 7A-7B can be stored in the controller for adjusting dipping parameters based on measured or predicted values. In some embodiments, the effect of ambient relative humidity and ambient temperature on viscosity and/or withdrawal speed can be accounted for by the controller, using correlations as described herein. In some embodiments, the coating solution can be chilled to produce thicker layers and/or to reduce solvent losses over time. The controller can select the chilled coating solution, if available, as an option for achieving a desired layer thickness for the next dip. In some embodiments, the wire status coming into the dip can be input, such as whether the wire is bare, or has another membrane already on it, and what that existing membrane thickness is all of which can impact the current dipping results. The algorithms can include heuristic algorithms such that the controller learns and improves control of the dipping process based on past dipping runs.

Figure 8:
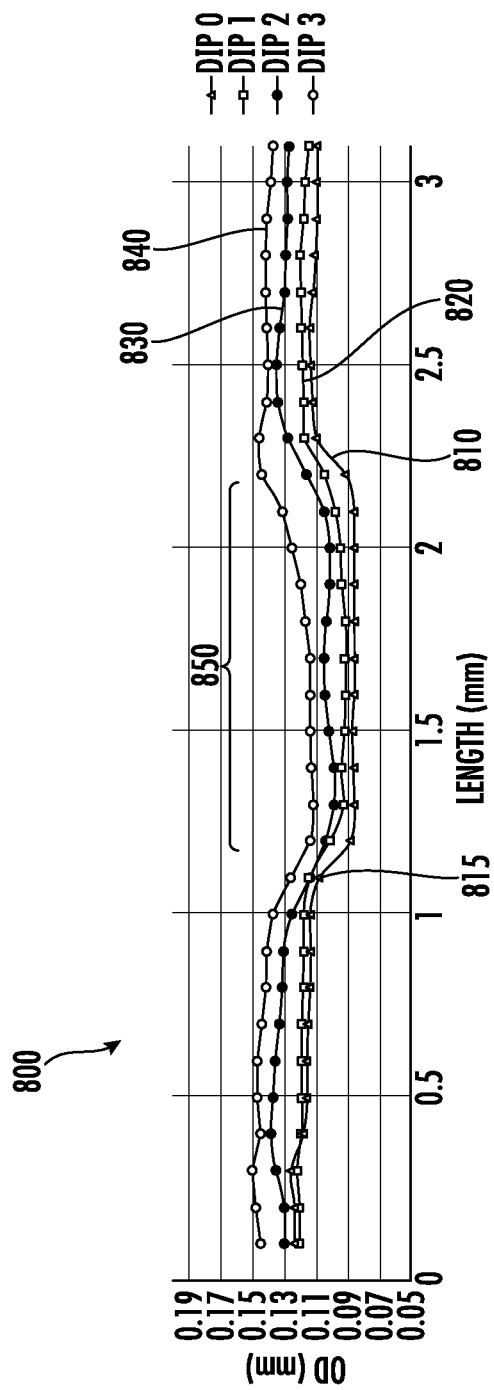
FIG. 8 is a graph of coated diameters along the length of a working wire, in accordance with some embodiments.

FIG. 8 is a graph 800 showing sample measurement profiles along a length of a wire as dipped layers were added. In this example, the substrate wire had an insulating polyurethane coating, onto which an interference membrane and enzyme membrane had already been formed. The region 850 from approximately 1.2 to 2.2 mm along the working wire (measured from the distal tip of the working wire) is a skived section where the insulation was removed, and thus the thickness values are lower in region 850 than the rest of the wire. The region 850 will serve as the active area of the working wire when the wire is assembled into a sensor. A first curve 810 ("dip 0") is the outer diameter (OD) in millimeters prior to any GLM layer dips being added. A second curve 820 is the OD after a first layer of the GLM membrane was coated on the wire, and curves 830 and 840 are for two subsequent dips. Each data point (e.g., data point 815 of curve 810) is an average of diameter measurements taken at three angular orientations by the automated measurement system (e.g., system 450 of FIG. 4B). FIG. 8 thus illustrates the numerous measurements that are taken along the wire by the automated measurement system, enabling thorough analysis of the dipping process. The measurements after each dip are used to adjust the dipping process parameters to achieve the target final thickness within a certain number of dips. The unequal distances between curves demonstrate the non-linear behavior in coating layer thicknesses as the layers are applied. For example, the layer thickness of the first dip (distance between curve 810 and 820) is generally less than the layer thickness of the third dip (distance between curve 830 and 840). The methods and systems of the present disclosure can compensate for these variations in real time, where the variations are often unpredictable due to the complex interactions between many factors of the dipping process and environment.

In embodiments, methods for coating a working wire for a continuous biological sensor include providing a plurality of wires in a fixture, and dipping the plurality of wires into a coating solution according to parameters for a dipping process. A plurality of diameters is measured, as an in-line process of the overall dipping process, along a length of at least two coated wires in the plurality of wires, using an automated measurement system. The methods also include determining, by a controller that is in communication with the automated measurement system, a thickness difference, the thickness difference being a difference between a thickness setpoint and an aggregate criteria for the plurality of diameters. Methods further include calculating, by the controller, adjusted parameters for the dipping process based on the thickness difference. The dipping may be performed again, using the adjusted parameters, based on the thickness difference, such as when the difference in thickness is greater than a target amount. In some embodiments, the adjusted parameters is further based on environmental factors, where the environmental factors may include an airflow velocity and a relative humidity of the airflow.

In some embodiments, determining the adjusted parameters comprises referring to a set of correlations, each correlation in the set of correlations comprising layer thickness as a function of withdrawal speed for a given viscosity of the coating solution. Methods may include determining the viscosity of the coating solution; and choosing a correlation in the set of correlations based on the viscosity. In some embodiments, determining the viscosity comprises measuring the viscosity of the coating solution. In some embodiments, determining the viscosity value comprises estimating a viscosity of the coating solution based on a relationship of solvent loss over time for the coating solution.

In some embodiments, the coating solution has a first viscosity, and the dipping process further comprises an additional coating solution having a second viscosity, the second viscosity being different from the first viscosity. Calculating the adjusted parameters comprises choosing the coating solution or the additional coating solution.

In some embodiments, calculating the adjusted dipping parameters comprises changing a withdrawal speed to minimize a number of dips for achieving the thickness setpoint within a target window. In some embodiments, calculating the adjusted parameters comprises reducing a total number of dips from a predefined number of dips to achieve a desired coating thickness or diameter. In some embodiments, the adjusted parameters comprise changing an orientation of the fixture during the dipping, from a previous coating iteration. In some embodiments, determining the thickness difference comprises setting an overall or aggregate target thickness, such as an average or median, for the plurality of wires, wherein the overall target thickness is within a target window of the thickness setpoint. In some embodiments, determining the difference in thickness comprises using a variance of the plurality of diameters, where the variance may be a lengthwise variance in a first coated wire in the at least two coated wires or a rotational variance in a first coated wire in the at least two coated wires. In certain embodiments, the variance comprises a difference in diameters between a first coated wire in the at least two coated wires and a second coated wire in the at least two coated wires, wherein the first coated wire and the second coated wire are mounted on different sides of the fixture from each other.

Reference has been made in detail to embodiments of the disclosed invention, one or more examples of which have been illustrated in the accompanying figures. Each example has been provided by way of explanation of the present technology, not as a limitation of the present technology. In fact, while the specification has been described in detail with respect to specific embodiments of the invention, it will be appreciated that those skilled in the art, upon attaining an understanding of the foregoing, may readily conceive of alterations to, variations of, and equivalents to these embodiments. For instance, features illustrated or described as part of one embodiment may be used with another embodiment to yield a still further embodiment. Thus, it is intended that the present subject matter covers all such modifications and variations within the scope of the appended claims and their equivalents. These and other modifications and variations to the present invention may be practiced by those of ordinary skill in the art, without departing from the scope of the present invention, which is more particularly set forth in the appended claims. Furthermore, those of ordinary skill in the art will appreciate that the foregoing description is by way of example only, and is not intended to limit the invention.

What is claimed is:

1. A method for coating a working wire for a continuous biological sensor, the method comprising:
   providing a plurality of wires in a fixture;
   dipping the plurality of wires into a coating solution according to parameters for a dipping process;
   measuring, as an in-line process, a plurality of diameters along a length of at least two coated wires of the plurality of wires in the fixture, using an automated measurement system;
   determining, by a controller that is in communication with the automated measurement system, a thickness difference, the thickness difference being a difference between a thickness setpoint and an aggregate criteria for the plurality of diameters; and
   calculating, by the controller, adjusted parameters for the dipping process based on the thickness difference.

2. The method of claim 1, further comprising dipping the plurality of wires using the adjusted parameters based on the thickness difference.

3. The method of claim 1, wherein calculating the adjusted parameters is further based on environmental factors.

4. The method of claim 3, wherein the environmental factors comprise an airflow and a relative humidity of the airflow.

5. The method of claim 1, wherein calculating the adjusted parameters comprises referring to a set of correlations, each correlation in the set of correlations comprising layer thickness as a function of withdrawal speed for a given viscosity of the coating solution.

6. The method of claim 5, further comprising:
   determining a viscosity of the coating solution; and
   choosing a correlation in the set of correlations based on the viscosity.

7. The method of claim 6, wherein determining the viscosity comprises measuring the viscosity of the coating solution.

8. The method of claim 6, wherein determining the viscosity comprises estimating an estimated viscosity of the coating solution based on a relationship of solvent loss over time for the coating solution.

9. The method of claim 1, wherein:
   the coating solution has a first viscosity;
   the dipping process further comprises an additional coating solution having a second viscosity, the second viscosity being different from the first viscosity; and
   calculating the adjusted parameters comprises choosing the coating solution or the additional coating solution.

10. The method of claim 1, wherein calculating the adjusted parameters comprises changing a withdrawal speed to minimize a number of dips for achieving the thickness setpoint within a target window.

11. The method of claim 1, wherein calculating the adjusted parameters comprises reducing a total number of dips from a predefined number of dips to achieve a desired coating thickness.

12. The method of claim 1, wherein the adjusted parameters comprise changing an orientation of the fixture during the dipping, from a previous coating iteration.

13. The method of claim 1, wherein determining the thickness difference comprises using a variance of the plurality of diameters.

14. The method of claim 13, wherein the variance comprises a lengthwise variance in a first coated wire in the at least two coated wires.

15. The method of claim 13, wherein the variance comprises a rotational variance in a first coated wire in the at least two coated wires.

16. The method of claim 13, wherein the variance comprises a difference in diameters between a first coated wire in the at least two coated wires and a second coated wire in the at least two coated wires, wherein the first coated wire and the second coated wire are mounted on different sides of the fixture from each other.

* * * * *